United States Patent [19]

McCleary et al.

[11] Patent Number: 5,250,306

[45] Date of Patent: Oct. 5, 1993

[54] DEBRANCHED ARABAN AND ITS USE AS A FAT SUBSTITUTE

[75] Inventors: Barry V. McCleary, North Rocks, Australia; Julian M. Cooper, East Dereham; Edward L. Williams, Costessey, both of United Kingdom

[73] Assignee: British Sugar PLC, Peterborough, United Kingdom

[21] Appl. No.: 689,866

[22] PCT Filed: Dec. 5, 1989

[86] PCT No.: PCT/GB89/01452
§ 371 Date: Jul. 15, 1991
§ 102(e) Date: Jul. 15, 1991

[87] PCT Pub. No.: WO90/06343
PCT Pub. Date: Jun. 14, 1990

[30] Foreign Application Priority Data

Dec. 5, 1988 [GB] United Kingdom ............... 8828378
Dec. 5, 1988 [GB] United Kingdom ............... 8828380

[51] Int. Cl.$^5$ ................................................ A23L 1/05
[52] U.S. Cl. ........................................ 426/52; 426/573; 426/804; 536/2
[58] Field of Search ............ 426/49, 50, 52, 51, 426/804, 330.5, 577, 573; 536/2

[56] References Cited

U.S. PATENT DOCUMENTS

| | | | |
|---|---|---|---|
| 2,803,567 | 8/1957 | Owens et al. | 127/34 |
| 3,737,322 | 6/1973 | Frey | 426/804 |
| 4,228,198 | 10/1980 | Burge | 426/656 |
| 4,672,034 | 6/1987 | Rombouts et al. | 435/101 |
| 4,794,013 | 12/1988 | Gresch | 426/51 |
| 4,816,078 | 3/1989 | Schiweck et al. | 127/36 |

FOREIGN PATENT DOCUMENTS

| | | |
|---|---|---|
| 0124439 | 4/1984 | European Pat. Off. . |
| 143261 | 4/1979 | German Democratic Rep. . |
| 2-154673 | 6/1990 | Japan ................ 426/590 |
| 2-21353 | 8/1990 | Japan ................ 426/573 |

OTHER PUBLICATIONS

Chemical Abstracts 95:23109t.
Chemical Abstracts 83:189627n.
Chemical Abstracts 75:142135v.
Chemical Abstracts 71:126265z.
Chemical Abstracts 68:88376q.
Chemical Abstracts 72:3681v.
Chemical Abstracts 108:163728f.
Chemical Abstracts 83:189627r.
Rouau et al., "Characterization and enzymic . . . ", pp. 439–443, 1987, United Kingdom.
Higashi et al., "Arabinan-degrading Enzymes . . . ", pp. 2903–2905 Agric. Biol. Chem., vol. 47(12), 1983.
Yasuda et al., "Decomposition of arabinan . . . ", pp. 109–117, 1980, Japan.
Waibel et al., "Purification of an . . . ", pp. 86–91, 1980 The Netherlands.
Stevens et al., "Structural Investigation of . . . ", pp. 559–561, 1980, United Kingdom.
Phillips et al., "Preparation, physical properties . . . ", pp. 451–460, 1992, United Kingdom.
Tagawa et al., "Preparation of L-Arabinan . . . ", pp. 542–546, Methods in Enzymology vol. 160.
Churms et al., "An L-arabinan . . . ", pp. 339–344, 1983, The Netherlands.

*Primary Examiner*—Carolyn Paden
*Attorney, Agent, or Firm*—Frost & Jacobs

[57] ABSTRACT

The polysaccharide araban is extracted from sugar beet by a novel modification of the known alkaline extraction process in which, after neutralization of the alkaline liquor, the liquor is ultrafiltered and the retentate is dried to obtain dry araban. Araban, obtained by the above process or otherwise, is incubated with α-L-arabinofuranosidase to cleave most or all of the branches from the araban. The debranched araban forms an aqueous gel which has the properties of a fat mimetic and may be used as a fat substitute in foods. Isolated debranched araban derived from crude sugar beet araban is a novel substance. Araban itself may be used in the novel applications of emulsification and encapsulation of oils, for example flavor oils.

21 Claims, No Drawings

DEBRANCHED ARABAN AND ITS USE AS A FAT SUBSTITUTE

FIELD OF THE INVENTION

The present invention relates to debranched araban. More particularly, the invention relates to a gel of debranched araban and to novel uses of debranched araban. The araban may be derived from sugar beet and the invention includes a method for the production of araban from sugar beet, as well as novel applications of araban.

BACKGROUND OF THE INVENTION

Arabans, also known as arabinans, are polysaccharides commonly found in pectic substances. Arabans, as present in cell-wall pectic substances, have been shown to consist of a main chain of 1,5-α-linked L-arabinofuranosyl residues to which other L-arabinofuranosyl residues are linked (1,3)-α and/or (1,2)-α in either a comb-like or a ramified arrangement. Arabans are found together with other pectic substances and, when extracted by normal techniques, arabans are obtained as crude product associated with other pectic substances. Arabans may be further purified to remove substantially all associated substances by chromatographic techniques, for example as described by Tagawa et al., *Carbohyd. Res.*, 11 (1969) 293-301. Typical crude beet araban residues contain about 70-85 wt. % arabinose, 5-10 wt. % uronic acids, 8-15 wt. % D-galactose, a few percent rhamnose and minor amounts of other monosaccharides. Purified araban normally contains no more than 2-3 wt. % of non-arabinofuranosyl residues.

It is already known to extract araban from sugar beet. For example, DD-A-143261 discloses that araban may be extracted from sugar beet material by heating the material in water in the presence of $Ca(OH)_2$ in an amount of 1-10% by weight based on the weight of beet material. The reaction mixture is maintained at 80°-100° C. for 10-120 minutes. L(+)-arabinose is then prepared by adjusting the pH of the mixture to 3 to 6. Sulphuric acid is added to the filtrate to a concentration of 0.2-3% and the araban is hydrolysed by heating the resultant solution at 80°-100° C. for 10-120 minutes. The reaction mixture is then neutralised and filtered.

Similarly, U.S. Pat. No. 4,816,078 and equivalent EP-A-276202 teach that crystalline L-arabinose may be produced from an araban-containing plant material by an extraction process using $Ca(OH)_2$. The plant material is solubilised by heating it at 105°-160° C. in a closed vessel in the presence of an aqueous medium containing 0.5-2 wt. % $Ca(OH)_2$, the $Ca(OH)_2$ being used in an amount of from 6-17 wt. % per kg. of dry matter. The cooled reaction medium is neutralised and filtered. The filtrate is condensed by evaporation and an araban-containing fraction is obtained using an ion exchange resin. The araban is hydrolysed with 0.5-2 wt. % $H_2SO_4$ at 92°-97° C. for 50-80 minutes and the reaction mixture is neutralised with $CaCO_3$, filtered and concentrated to 40-60 wt. % dry matter by evaporation. A fraction containing L-arabinose is separated using an ion exchange resin. The arabinose-containing fraction is concentrated to 60-80% dry matter and cooled to crystallise out the arabinose.

The extraction of araban from beet pulp using $Ca(OH)_2$ is also described by Tagawa et al., *Methods in Enzymology*, Vol. 160, Part A (1988), 542-545. Tagawa purifies the crude araban by chromatography.

Debranched araban is also a known class of material. Hitherto, it has been known principally as an undesirable constituent of fruit juices. The yield of fruit juice from apples and pears can be dramatically improved by the use of enzymes to degrade pulp polysaccharides and by more exhaustive extraction of the pulp with diffusion equipment. These processes significantly increase the amount of partially degraded polysaccharide which is solubilised. Changes in temperature or pH after extraction can lead to the precipitation or crystallisation of the partially degraded polysaccharide. Such precipitation or crystallisation gives rise to "hazy" fruit juice, which is unwelcome in the preparation of clear juices. A haze material identified in apple and pear juices is "essentially linear" 1,5-α-L-arabinan (Churms et al. (1983) *Carbohyd. Res.* 113, 339-344).

Churms isolated the linear L-arabinan by a process in which crude product was obtained by centrifugation and then purified by twice dispersing it in distilled water and centrifuging. The crude product was found to contain only traces of hexoses and uronic acid in addition to arabinose, whilst the purified product contained L-arabinose only. (Apple juice arabans consist almost entirely of arabinose).

It is now generally accepted that the problem of linear araban haze should be dealt with by treating the fruit pulp with pectinase enzyme preparations containing high levels of both α-L-arabinofuranosidase and endo-1,5,-α-L-arabinanase. The arabinofuranosidase cleaves the 1,3-α- and 1,2-α- linked L-arabinosyl branch units, allowing ready access of the 1,5-α-L-araban main-chain to depolymerisation by the endo-arabinanase. The implementation of this technology, however, requires the measurement of endo-arabinanase in pectinase preparations. The substrate generally employed is linear 1,5-α-L-araban (Voragen et al., (1987) *Food Hydrocolloids* 1,423-437) which is removed by filtration of "hazy" fruit juice concentrates.

Voragen describes a study in which the activity is investigated of a number of arabinanases when incubated with different substrates. The substrates include beet araban (highly branched), apple juice ultrafiltration retentate (UFR) araban (intermediately branched) and haze araban (linear). Voragen does not indicate that he prepared highly debranched or linear araban from beet araban and the isolation of debranched beet araban is not described. It can be inferred from Voragen that 100% debranched apple araban was not isolated, although product with a lower level of debranching was apparently isolated. Voragen does describe the isolation of arabin furanosidase enzymes.

The preparation of linear araban (1,5-α-L-araban) from purified beet araban using α-L-arabinofuranosidase is described by Tagawa et al. *Carbohyd. Res.*, 11 (1969) 293-301. The crude beet araban used by Tagawa was purified from 73.7% L-arabinose content to 97.8% L-arabinose content, whilst the debranched material contained 98.3% L-arabinose. Tagawa does not specify the degree of debranching but it may be inferred that it was probably close to 100%. In this paper, Tagawa et al. also describe a method for the isolation of α-L-arabinofuranosidase from a culture filtrate of *Aspergillus niger*.

All references referred to above are incorporated herein by reference.

SUMMARY OF THE INVENTION

We gave now found that debranched araban is useful as an ingredient in foodstuffs and pharmaceuticals, especially as a fat-substitute. More particularly, when sufficiently debranched, araban forms a gel which has the properties of a fat mimetic useful in foodstuffs and pharmaceuticals, for example. Araban may be bleached or otherwise decolorised to form a lighter-coloured product than the native substance. Low colour debranched araban may be prepared using decolorised araban.

In one aspect, the present invention provides an aqueous gel of debranched araban. The araban may be totally or partially debranched, and experiments indicate that, in order to be gel-forming, debranched araban should usually be over 80% debranched. When applied to the present invention, the term "debranched araban" signifies a gel-forming product. Preferably the araban is at least 85% debranched and it may be 90 or 95% debranched. The araban is more desirably at least 95% debranched and most preferably is substantially totally debranched araban (e.g. at least 98% or 99% debranched). Araban which is substantially totally debranched may conveniently be referred to as "linear araban". 100% Debranched araban is especially preferred.

The debranched araban may be, and preferably is, derived by debranching crude araban rather than purified araban; such debranched araban derived from crude araban is associated with other pectic substances and/or their derivatives.

As to whether debranched araban forms a gel depends in part upon the degree of debranching and the concentration of the debranched araban. Gel formation is believed also to depend on the constituents of the araban used and upon other constituents in the aqueous medium. Whilst it is not possible to specify the precise combinations of properties required for gel-formation, we have found that a minimum debranched araban content of 8% by weight based on the weight of the gel is normally required and that a content of 12 to 20 wt. % is most preferred. It is preferred that the debranched araban be present in an amount of no more than 30% by weight, more preferably no more than 254 by weight of the gel.

The concentration of debranched araban used will depend upon the properties of the material itself and the desired characteristics of the gel.

The gel has yield and flow properties similar to those of semi-fluid systems such as creams and spreads. The gel is therefore useful as a food ingredient, particularly as a fat-substitute, as is debranched araban itself. Such use is included in the invention.

The gel may be prepared by warming debranched araban in water to a temperature at which the solid dissolves, for example a temperature of more than 55° C., preferably more than 60° C., and then allowing the solution to cool and stand until a gel forms. Normally, the solution must stand for at least several (e.g. 2 to 3 or more) hours for a gel to form. The gel may take up to two days to reach maximum strength. Optionally, the solution may be heated to 100° C. to kill any microorganisms.

The gel of the invention preferably contains a debranched araban derived from an araban referred to herein, e.g. sugar beet araban, especially crude sugar beet araban. The araban may be extracted by the method of extraction described herein.

The debranched araban is preferably prepared from sugar beet araban or, less preferably, from other varieties of *Beta vulgaris*, for example fodder beet, as well as from other plants. The preparative process may be performed by contacting araban with an α-L-arabinofuranosidase, that is, an enzyme which cleaves (1,3)-α and (1,2)-α linkages between arabinose residues.

We have prepared and isolated debranched araban from crude beet araban containing typically from 70-85 wt. % arabinose, although exceptionally the arabinose content might be higher, e.g. 90%. The arabinose content in the debranched product is broadly similar to that in the starting material, although usually slightly less, for example up to 5% less than in the starting material. The isolation of debranched araban containing up to 90 wt. % arabinose units is novel. Usually, the arabinose content in debranched crude beet araban is no more than 85 wt. % and most typically is from 65 to 80 wt. %.

Hitherto, the only debranched araban which has been isolated in solid form has contained only about 2% or less of residues other than arabinose units. Accordingly, a further aspect of the invention resides in gel-forming debranched araban in purified or solid form of which no more than 90 wt. % is arabinose. The isolation in the solid state of gel-forming debranched araban derived from crude sugar beet araban is also novel and included in the invention. Such isolated debranched arabans are preferably linear.

Also novel, in the solid state, is gel-forming, debranched, non-linear sugar beet araban. By way of example, non-linear araban may be up to 97% debranched or, in another embodiment, up to 95% debranched.

DETAILED DESCRIPTION OF THE INVENTION

Unless otherwise indicated, degrees of debranching referred to herein are as determined by proton resonance nmr. This technique is illustrated in Example 2c below.

Illustrative procedures, uses and products will now be described by way of example only.

1. Preparation Debranched Araban a. Isolation of Arabinofuranosidase

Arabinofuranosidase may be isolated from culture filtrate of *Aspergillus niger* (see Tagawa et al., Supra) or from commercial pectinase mixtures, for example "Ultra SP" made by Novo Enzymes. The separation of an enzyme from an enzyme mixture is a known technique, described for example by Tagawa, and need not be described at length. The purification may be conducted using ion-exchange and gel filtration chromatographic procedures. In an exemplary procedure Ultra SP is applied to a column of DEAE-Sepharose ® Fast Flow (cation exchanger) which is connected to a fraction collector and fractions are collected. The eluate is assayed for arabinofuranosidase (AF) activity using p-nitrophenyl-α-L-arabinofuranoside as substrate; this substrate releases phenolate when digested with AF and the colour of the phenolate may be developed by the addition of an alkaline solution, for example trizma base. Trizma base is a reagent supplied by Sigma Chemicals. The AF-containing fractions are chromatographed on Ultrogel ® AcAS4 (gel filtration) and the resultant fractions are rechromatographed on DEAE Sepharose ® Fast Flow (cation exchanger). This process produces AF free of endo-arabinanase.

b. Preparation of Debranched Araban from Sugar Beet Araban

The debranching of the araban is performed simply by incubating the araban with AF. The relative proportions of the enzyme and substrate, the duration of the incubation and the incubation temperature must be selected to obtain gel-forming (e.g. greater than 80% debranched) debranched araban. The conditions may be selected by trial and error, but we have found that 150 Units of AF release about 50% of the arabinose branches of a 100 g sample of araban in 20 hours at 40° C. and pH 4.

The debranched araban may be precipitated from the mixture, optionally after inactivation of the AF (e.g. by heating to at least 80° C.), and further purified. A suitable method of precipitating the debranched araban is the addition of ethanol and saturated aqueous KCl to the mixture. The purified product may be freeze dried.

2. Formation of Debranched Araban Gel

An aqueous mixture of the debranched araban is heated to dissolve the solid. A temperature of greater than 55° C. and more usually of greater than 60° C. is normally appropriate for dissolving the solid. The resultant solution is allowed to cool and to stand, e.g. for 2-3 hours, to permit a gel to form. The mixture might have to stand for a longer time, e.g. up to 2 days, if the gel is to reach maximum strength. An increasing level of debranching and an increasing debranched araban concentration both promote gelling; a suitable combination of level of debranching and concentration for any desired gel characteristics may be determined by routine empirical experimentation. We have found that a debranched araban concentration of 15% by weight of the gel is very satisfactory and a level of 12-20% is most preferred. Normally, not less than 8% debranched araban is used and more preferably not less than 10%, whilst it is envisaged that a maximum concentration of 25% or 30% by weight of the gel will not usually be exceeded.

If necessary, the starting mixture may be boiled to kill microorganisms.

It may be found in isolated instances that a gel is not formed even when normally gel-forming conditions are used. In such a case, the debranched araban may be discarded and a fresh batch used. The suitability of any batch of linear araban for use as a fat-substitute may be tested by ascertaining whether a sample from the batch forms a gel. One possible cause of non-gelling might be that the araban is insufficiently debranched, in which case the araban could be re-incubated with AF and the original incubation conditions should be adjusted to increase the degree of debranching.

The gel is relatively pH stable and we have found it stable at a pH of as low as 3 as well as at moderately alkaline pH. The gel and the starting mixture may, therefore, contain constituents other than water and debranched araban, so long as the constituents do not significantly interfere with gel-formation or gel stability.

3. Decolorising of Araban for Preparation of Low Colour Debranched Araban

Debranched araban derived from crude sugar beet araban forms a gel which is mid-brown in colour and is therefore unsuitable for many applications. A much lighter coloured product may be made by decolorising the araban prior to its incubation with AF. Optionally, the araban may be decolorised as part of its extraction process. The decolorising may be conducted by bleaching the araban, e.g. with hydrogen peroxide. The preferred conditions for bleaching are with hydrogen peroxide at neutral or slightly alkaline pH (e.g. pH 8.5) at 75° C. for 0.5 to 2 hours, to give 75% colour removal. As less preferred bleaches there may be mentioned sodium hypochlorite, sodium borohydride and a sulphite solution sold under the trade mark Hydros. When bleaching the supernatant remaining after the neutralisation step in the araban extraction process, we have found that hydrogen peroxide may suitably be used in an amount of 0.2 to 0.5% (w/w) based on the supernatant (equivalent to about 5-25% by weight of the araban content). Treatment with membranes or decolourising absorbants is less effective, but may be used. If desired, a combination of decolorising techniques may be used.

4. Use of Debranched Araban

Debranched araban has properties in gel form which mimic those of fats, and may thus be used as a fat or oil substitute. As a carbohydrate, the product is substantially less calorific than fats: fats have about 9 calories per gram (about 38 kJ/g) and we estimate that debranched araban has only about 2 calories per gram on a dry basis (about 8.5 kJ/g). Debranched araban, that is, araban debranched sufficiently to form gels, is therefore useful as a low energy fat or oil substitute in foods and beverages. It may also be used as a bulking or binding agent in foods and beverages, or as an extrusion aid or flow aid. The debranched araban may likewise be used in preparations for foods or beverages.

The preferred debranched araban is derived from sugar beet araban, especially crude sugar beet araban containing no more than 90 mole % arabinose and more usually from 70 to 85 mole % arabinose.

A number of carbohydrate products are already on the market as fat/oil replacers, e.g. those sold under the trade marks PASELLI SA2 (Avebe b.a., Foxhol, Netherlands) and AVICEL (FMC, Philadelphia, U.S.A.). In principle, debranched araban may be used in the same applications as such existing products.

Specific applications envisaged for debranched araban include:
spreads (low fat butter substitutes)
bulking agent or fat substitute in bakery products or mixes therefor
fat replacement in ice creams
fat replacement in confectionery, e.g. toffee
fat replacement or bulking agent in desserts, toppings, icings and fillings, and mixes therefor
fat replacement in sauces, mayonnaise, salad dressing, pickles
flow aid or fat replacement in cheese or cheese spread
fat replacement in paté or in fish or meat pastes
fat replacement or bulking agent in dips
extrusion aid or fat replacement in savoury snacks or snack fillings
cream replacer in drinks
dietary fibre source in foods
use in frozen food
property modifier (combined spreading and melting properties) in marinades.
emulsifier It is also envisaged that the product would find application in non-food materials (especially oily or creamy materials), e.g. toiletries, cosmetics and pharmaceuticals, e.g. as a bulking or binding agent.

We have found linear araban to be an effective fat or oil substitute when incorporated in food mixes either in the form of a pre-made gel or in the form of a powder which is dissolved in the mix. It has been found that, in products which contain a substantial quantity of water in addition to the gel, an acceptable product can be obtained in some circumstances where the linear araban concentration calculated on the basis of the total water content is below that apparently necessary for gel formation; specifically, we have observed this phenomenon in products containing other water-absorbing constituents, for example, gums or gelatin. Suitable quantities and combinations of ingredients for any product can be determined by trial and error, but our experiments indicate that replacement of 50% of the oil or fat of a conventional product with a linear araban gel can often produce an acceptable product.

5. Preparation of Araban from Sugar Beet

The method of preparation is not critical to the production of debranched araban and any known process may be used, for example. The extraction of araban under alkaline conditions is well known and requires no further description here. However, we have devised a novel process for preparing araban which provides an economical route to a relatively pure product.

Our new process is a modification of the known alkaline extraction process and is characterised in that, after neutralising the alkaline extractate (liquor containing extracted araban), the liquor is ultrafiltered, to both purify and concentrate the liquor, and the retentate may then be dried. The extraction process itself preferably comprises adding sufficient water to beet pulp to form a mobile slurry, treating the slurry with calcium oxide or hydroxide at a temperature of at least 70° C. and pressing the slurry to separate extract therefrom. Preferably, the neutralising agent is carbon dioxide. If desired, the araban may be decolorised prior to being dried, e.g. before ultrafiltration.

The beet pulp used in the extraction process is a by-product from the extraction of sucrose from beet. It is preferred to use wet or pressed pulp. Wet pulp is the pulp remaining after extraction of the sucrose-containing liquors. Pressed pulp is wet pulp after pressing. Wet pulp typically contains about 8% by weight of dry matter and pressed pulp typically contains about 25% by weight of dry matter. It is, however, possible to use a dried pulp as starting material. High temperature dried pulp gives a poor yield, but pulp dried at a lower temperature, as on a fluidised bed, and steam dried pulp both give good yields.

Water is added to the beet pulp, whether wet or pressed or dried, to form a mobile slurry. The weight of water added to pressed pulp is suitably from 0.75 to 5 times the weight of the pressed pulp. Less than that amount of water may not make the resultant slurry sufficiently mobile, whereas too much water is uneconomic, both because of the need to heat it and the eventual need to remove it from the ultimate product. As noted above, pressed pulp contains only about 25% by weight of dry matter, so that if the starting material is a dried pulp correspondingly larger amounts of water will be necessary. Similarly, correspondingly smaller amounts of water will be necessary when wet pulp is used as the starting material The slurry is then normally heated to at least 70° C., preferably to 90° C. and more preferably to from 95° C. to 98° C. Calcium oxide is then added, suitably in an amount of from 30 to 70 g per kg of pressed pulp (correspondingly larger amounts per kg of dried pulp), and the mixture is agitated, preferably for 15 to 90 minutes, while maintaining the aforesaid temperature. Temperatures below 70° C. were found to give a liquor that could not be carbonatated so effectively.

The liquor is then expressed from the slurry, and is suitably combined with washings from the remaining solid matter. The basic liquor is then neutralised. This step may be performed by addition of an acid forming a soluble calcium salt, e.g. hydrochloric, acetic or nitric acid, or of an acid forming an insoluble calcium salt, e.g. phosphoric or sulphuric acid. However the preferred neutralising agent is carbon dioxide. The neutralisation preferably proceeds until the pH is from 7 to 9, more preferably 8, and the resultant calcium carbonate (when carbon dioxide is used) settles. pH values are given after conversion to 20° C., although the neutralisation is effected at a temperature of at least 60° C. and preferably 80° C.

The neutralised liquor may be check filtered to remove large particles which might foul the ultrafiltration membrane in the subsequent ultrafiltration. A plate and frame press or a cartridge filter is suitable. The liquor may at this stage optionally be decolorised, for example if it is desired to use the araban to prepare low colour debranched araban.

The liquor is then passed through an ultrafiltration membrane. The ultrafiltration will be performed at a temperature at which the liquor has an acceptable viscosity, a temperature of at least 40° C. being usual. The temperature should, however, not exceed the manufacturer's recommended maximum temperature for the membrane. A membrane having a nominal molecular weight cut off of 10,000 is most suitable. A membrane having a nominal molecular weight cut off of 5,000 or less may require too much pressure to be practical, whereas a membrane having a nominal molecular weight cut off of 30,000 or more may cause too much of the product to be lost. However, the optimum molecular weight nominal cut off may be different for different membrane types. The nominal molecular weights of ultrafiltration membranes are calculated for proteins; as will be seen hereinbelow the araban which is retained by the membrane has a considerably higher molecular weight due to the different radii of polysaccharides. Prior to ultrafiltration the araban concentration in the liquor may be about 2%-4% by weight, but the retentate may contain about 20% araban by weight. The ultrafiltration is performed principally to remove calcium salts, especially calcium acetate. It also removes other low molecular weight impurities, e.g. sucrose, and water.

Decolorisation may additionally or alternatively be performed after ultrafiltration.

The retentate may then be dried to give the product araban as a powder of from about 90 to 95% dry weight. Drying is suitably effected by evaporation to about 35% araban by weight, followed by spray drying. If the araban is to be treated with AF to be debranched, the retentate may be treated directly with AF after pH adjustment to pH 4 to 4.5, instead of being dried.

The resultant araban is a branched polysaccharide containing about 80% of L-arabinose, other neutral sugars (D-galactose, about 15%; L-rhamnose, about 5%, D-xylose, D-glucose and D-fructose, less than 1% each), and polygalacturonic acid. It has a molecular weight of about 50,000. The product is commercially acceptable at this degree of purity. The composition is not markedly affected by variations in the starting material (location of beet growth or variants of beet).

6. Uses of Araban a. General Discussion

Araban has viscosity characteristics which make it useful as a confectionery base, e.g. in fruit gums and in pastilles, or as a binder in pharmaceuticals or in any tablet.

We have now found that araban has surface active properties which make it suitable for use as an emulsifying agent. It has also been determined that, quite unexpectedly, oily substances (e.g. flavours and fragrances) may be encapsulated using araban and that such encapsulated substances have a markedly longer shelf life than those encapsulated with the conventional encapsulant, gum arabic.

Gum arabic, an exudate of *Acacia senegal*, has been used since the 1930s as the major encapsulating agent for flavour oils, principally for use by the soft drinks industry. Recent years, however, have seen increasing difficulties of supply due to adverse climatic condition in the main producing countries, such as Sudan. Over the past decade, the consumption of gum arabic generally has roughly halved due to limited supply and increased prices. Current prices are around £4,000 per tonne. These difficulties have occurred at a time when the soft drink industry has been steadily expanding, and suitable replacements for gum arabic have been sought. The starch industry has responded to this demand and several starch products for use as encapsulating agents have been developed and marketed. The prices of these lie in the range £2,000–£3,000 per tonne depending on type. Whilst these have gained some acceptance by the industry, they are not wholly suitable as complete replacers of gum arabic but are more frequently used in conjunction with gum arabic. A demand for gum arabic replacers in spray-dried encapsulated products therefore remains.

b. Novel Uses of Araban

The use of araban as an emulsifying agent, e.g. for citrus oils, and its use as an encapsulating agent for flavours and fragrances or other oils are both new and form part of the present invention. The invention also includes an aqueous emulsion of araban and a fat or oil. The oil or fat may be citrus oil or another fragrance or flavour. The araban preferably constitutes from 20 to 50%, more preferably from 30 to 40%, by weight of the aqueous phase. The fat or oil preferably constitutes from 10 to 30%, more preferably 15 to 20%, by weight of the emulsion. Further included in the invention is an oil or fat encapsulated in araban. The encapsulated oil or fat may be prepared by forming an aqueous emulsion of araban and the fat or oil and spray drying it.

Araban may be used as an emulsifying agent for oils or fats, especially essential oils such as a citrus oil or another flavour or fragrance, for example, by forming an aqueous dispersion of araban powder in water. The dispersed solid may be allowed to dissolve more fully before further use. An emulsion may then be prepared by addition of an oil, e.g. citrus or another essential oil, or a liquid fat to the aqueous composition under constant agitation and by subsequent homogenisation of the mixture.

The emulsified oil, e.g. a soft beverage flavouring material, may then be encapsulated by spray-drying the emulsion. The encapsulation efficiency of araban has been found to be similar to that of gum arabic. However, araban encapsulated oil is considerably more stable during storage than gum arabic encapsulated oil. After 28 weeks storage, the loss of oil from sample araban encapsulated oil has been shown to amount to only about 10% to about 45% of the loss from comparable gum arabic encapsulated oil.

The araban used as an emulsifier or encapsulant is preferably an araban referred to herein, e.g. sugar beet araban, especially crude sugar beet araban. The sugar beet araban is preferably prepared by or preparable by the preparative method of the invention.

EXAMPLES

In the Examples, all percentages are by weight unless otherwise indicated.

EXAMPLE 1

Purification of arabinofuranosidase from Ultra-SP (USP)

USP (120 ml) is diluted to 500 ml in 20 mm Tris/HCl buffer (pH 8.0) and the PH is adjusted to 8.0. This solution is applied to a column of DEAE-Sepharose ® Fast Flow (3.5×23 cm) and the column washed with 20 mM Tris (pH8, 1 liter) and then with a KCl gradient (0→0.5M, total volume 4 liters) in 20 mM tris/HCl (pH 8.0).

The column is connected to a fraction collector when the gradient elution is started, and fractions of 380 drops/tube (approx. 21 ml/tube) are collected.

The column eluate is assayed for AF activity using p-nitrophenyl-α-L-arabinofuranoside (5 Mm) as substrate. The assay is further described below. Fractions active in AF are combined and are adjusted to pH 4.5 by addition of 1 molar acetate (pH 4.0) and solid ammonium sulphate is added at a rate of 60 grams/100 ml. This is dissolved and the solutions left at 4° C. for 16 hours. The resultant precipitate is recovered by centrifugation (12,000 rpm, 10 min.) and the pellets are dissolved in a minimum volume of distilled water and stored at 4° C.

This solution is chromatographed on Ultrogel ® AcAS4 (column 4.5×90 cm) and the fractions active in AF are combined. The pH is adjusted to 8.0 with tris/HCl buffer and the solution is then rechromatographed on DEAE-Sepharose ® Fast Flow.

Standard Assay for Arabinofuranosidase (AF)

0.1 ml of p-nitrophenyl α-L-arabinofuranoside is prepared in 0.1M acetate buffer (pH 4.0).

Add 0.1 ml of suitably diluted enzyme. Incubate at 40° C. for 2 minutes. Stop reaction and develop colour of released phenolate by the addition of 3.0 ml of 24 trizma base (pH~11.0). Read absorbance (ΔA) at 410 nm.

Calculation of Activity:
Units ml (undiluted enzyme)

$$= \frac{\Delta A}{\text{Incubation time}^b} \times \frac{3.2^b}{0.1^c} \times \frac{1}{17.8^d} \times \text{Dilution}$$

-continued $$= \frac{\Delta A}{2} \times \frac{3.2}{0.1} \times \frac{1}{17.8} \times \text{Dilution}$$

$$= \Delta A \times 0.899 \times \text{Dilution}$$

[a] Volume of assay mixture.
[b] Incubation time = 2 minutes.
[c] Volume of aliquot assayed.
[d] Molar extinction of p-nitrophenol.

EXAMPLE 2

Preparation of Debranched Beet Araban

Example 2a

Preliminary Experiment

In Example 2a the rate at which arabinofuranosidase (AF) releases arabinose is determined. This information is of assistance in selecting the amount of AF and the duration of incubation required to obtain a given degree of debranching.

To 10 ml of 10% beet araban in 0.05M sodium acetate buffer (pH 4.0), add 5 units (on p-nitrophenyl α-L-arabinofuranoside) of AF (0.5 ml) and incubate at 40° C. Take 0.5 ml aliquots at 0, 15, 30, and 60 min. and stop the reaction by heating at 100° C. for 2 min. Dilute these samples to 10 ml and remove 0.5 ml aliquots for Nelson/Somogyi reducing sugar determination.

Calculate the amount of arabinose equivalents (mg) released per hour per 1 unit of enzyme:

$$\frac{\text{absorbance (60 min.)}}{5 \text{ (units of } AF)} \times \frac{50 \text{ (}\mu g \text{ of Arabinose)}^a}{\text{Absorbance for 50 }\mu g \text{ of Arabinose}} \times$$

$$\frac{10.5^b}{0.5^c} \times 20^d \times \frac{1^e}{1000}$$

[a] Factor to convert from absorbance value for arabinose to micrograms of arabinose (Nelson/Somogyi reducing sugar method, Standard Solution).
[b] Final volume is 10.5 ml.
[c] Aliquot removed for dilution is 0.5 ml.
[d] An aliquot of 0.5 ml is removed from 10 ml of diluted sample.
[e] $\frac{1}{1000}$ — conversion from micrograms to milligrams.

$$= \frac{\text{absorbance (60 min.)}}{5} \times \text{Arabinose Factor} \times \frac{420}{1000}$$

$$= \text{absorbance (60 min.)} \times \frac{\text{Arabinose Factor}}{5 \text{ (units)}} \times \frac{20}{1000}$$

e.g. 5.3 mg released/hour/1 unit, or 106 per unit in 20 hours.

One liter of 10% araban = 100 g.

The maximum degree of hydrolysis of this araban is 31%, i.e. 31 grams of arabinose released per 100 grams of araban.

Thus 150 units will release approximately 150 × 106 mg = 15.9 grams in 20 hours. This is 15.9/31 × 100 = 51.3% of the arabinose branches.

Example 2b

Preparation of Debranched Araban

Samples of beet araban (10% w/v) were incubated with AF as follows:
L. 1 liter plus 0.5 ml of AF at 148 U/ml for 16 h.
M. 2 liters plus 2.0 ml of AF at 148 U/ml for 16 h.
N. 2 liters plus 4.0 ml of AF at 148 U/ml for 16 h.
T. 200 ml plus 2.0 ml of AF at 148 U/ml for 16 h.

After incubation, 0.2 ml aliquots were diluted to 10 ml with water and Nelson/Somogyi assays were performed on 0.2 ml aliquots. Absorbance values were as follows:

| Sample | ml enzyme/ liter | Absorbance (520 nm) | Debranching (%) |
|---|---|---|---|
| Original | 0.0 | .083 | 0 |
| L | 0.5 | .268 | 28 |
| M | 1.0 | .444 | 55 |
| N | 2.0 | .643 | 85 |
| Totally Debranched (T) | 10.0 | .743 | 100 |
| Arabinose/50 μg = .497 | | Blank = .042 | |

The bulk solutions were then heated to 80° C. to inactivate the enzyme, and cooled to room temperature. The solutions were then treated with 4 volumes of ethanol and 50 ml of saturated KCl and allowed to stand at room temperature for 20 hours. The residues were then recovered on a sintered glass funnel under vacuum. The residue was resuspended in ethanol and homogenised. It was then recovered by filtration, washed with ethanol and dried in a freeze drier.

| | RECOVERIES: | | |
|---|---|---|---|
| | RECOVERY | | |
| SAMPLE | (g) | (%) | GRADE |
| L | 78.5 | 78.5 | A1 |
| M | 149.0 | 74.5 | A1 |
| N | 142.1 | 71.0 | A1 |
| T | 13.0 | 65.0 | A1 |

Example 2c

Result of Proton Resonance nmr

On analysis by proton resonance nmr, the $H_1$ of 1,5-linked arabinose gave peaks at approx. 5.00 ppm. The $H_1$ of 1,3-linked arabinose, gave peaks at 5.07 ppm. Native araban gave peaks at these two resonances, whereas linear araban from fruit juice (Novo) only gave peaks at 5.00 ppm.

Treatment of native araban with AF gave a progressive reduction in the peak intensity at 5.07 ppm compared to that at 5.00 ppm. The change in this ratio can be used as an indication of the percentage removal of 1,3-linked arabinofuranosyl residues. The results obtained for samples L, M, and N are shown below.

| SAMPLE | Ratio of Peak Heights (1,3/1,5) | Degree of Debranching (%) |
|---|---|---|
| Native Araban | 1.09 | 0 |
| Partially Debranched | | |
| L | 0.73 | 33 |
| M | 0.45 | 59 |
| N | 0.22 | 80 |
| Totally Debranched | 0.005 | 100 |
| Linear Araban (Novo) | 0.01 | 99 |

$$\text{Debranching (\%)} = \frac{\text{Ratio 1,3/1,5 for Native} - \text{Unknown}}{\text{Ratio 1,3/1,5 for Native} - \text{Totally Debranched}}$$

The above values are in reasonable agreement with those estimated from the reducing sugar values on AF treatment.

EXAMPLE 3

Preparation of Debranched Araban Gel

The gelling and solubility properties of two samples of debranched araban with degrees of debranching of respectively 70–80% and 100% were studied.

a. Solubility Studies

20% (w/w) solutions of both materials were prepared in distilled water containing 0.05% (w/v) sodium azide to prevent microbiological activity. Their degree of solubility was recorded. Insoluble samples were heated in a water bath and the temperature at which the samples completely dissolved was noted.

b. Gelling Properties

Two batches of 100% debranched araban at 20% (w/w) were prepared by stirring the powder and distilled water together. After hydration of the batches for 2 hours, they were heated in a water bath to approx. 90° C. For each batch, 4×7 ml samples were taken in disposable plastic containers. These were matured at 10° C. for 17 hours.

The samples were then tested on a Stevens-LFRA Texture Analyser.

Texture profile curves were obtained for the samples. These gel samples were melted in a water bath (approx. 90° C.) and re-matured at 3° C. for 17 h. Texture profile analyses were again made on these gels. This procedure of testing/melting/re-maturing was repeated for the following temperatures and times, that is. 25° C./17 h; 10° C., 3° C., 25° C. for 3 h; 10° C., 3° C., 25° C. for 66 h.

The gel properties of four concentrations at 10° C. and 25° C. (maturation time, 17 h) were measured on the Stevens-LFRA Texture Analyser. The concentrations were 14%, 16%, 18% and 20%.

For each sample, 3 gels were prepared as described previously and matured at 10° C. for 17 h. Samples were tested on the Stevens penetrometer, melted and re-matured at 25° C. for 17 h and tested again.

c. Microscopy Studies

Three gels of 100% debranched araban (20% w/w) were each melted and matured at 3°, 10°, 250° C. for 17 h. These samples were examined by light microscopy and transmission electron microscopy.

RESULTS a. Solubility Studies

The 70–80% debranched sample was soluble in cold water at 20% (w/w) to give a dark brown solution which was not particularly viscous. More powdered material was added to the 20% solution to give a final concentration of 38%. A viscous solution (not paste like) was produced which had a grainy appearance—this dissolved on heating. This sample did not set or gel on cooling.

The sample of 100% debranched araban dispersed with difficulty in cold water at 20% concentration to produce a light brown stiff paste. This dissolved at about 70°–75° C. to give a brown solution.

b. Gelling Properties

The 100% debranched araban produced firm pastes after maturation at 3°, 10° or 25° C. for at least 3 hours.

Gel structure was found to develop over a period of hours. Gels matured at 3°, 10° and 25° C. have rigidities and break strengths which are similar but which show a significant fall with increasing maturation temperature. This suggests that it is the fine network material which is primarily responsible for gel strength. The dependence of gel strength on araban concentration is pronounced as one might expect in a close-packed microfibrillar network. The sample formed useful gels in the concentration range 14–20%.

c. Microscopy Studies

The 100% debranched araban formed a network of microfibrils upon maturation. The microfibrils appear to form a randomly oriented, three-dimensional cage structure within which water is effectively trapped. This network is responsible for the rigidity, yield and flow properties of the araban-water system.

EXAMPLE 4

Decolorising of Araban

10 Liters were taken of the supernatant juice obtained in the araban production process after carbonatation (carbon dioxide addition to neutralise the solution and to precipitate calcium). The supernatant juice was transferred to a stainless steel bucket and 40 ml of 60% hydrogen peroxide solution was added to give 0.24% hydrogen peroxide based on the juice. The juice was maintained at 75° C. for one hour and cooled to about 30° C. A small sample was removed for analysis and the remainder was passed on to the ultrafiltration stage.

The colour of the sample was measured by absorption, after adjustment to pH 7 and filtration through 0.45 μm membrane filter, on a spectrophotometer at 420 nm in a 1 cm width glass cell. The refractometric dry substance (RDS) of the solution was measured and the colour quoted as specific absorbance index (SAI), where $$SAI = \frac{absorption \times 100,000}{RDS}$$

| Sample | pH (not adjusted) | Absorbance | RDS | SAI |
|---|---|---|---|---|
| Juice before: | 7.5 | 1.035 | 3.2 | 32340 |
| Juice after: | 6.8 | 0.366 | 3.4 | 10760 |

Decolorising = 67%

EXAMPLE 5

Preparation of Foodstuffs using Debranched Araban

Recipes a. and b. use a gel containing linear araban in an amount of 13% by weight based on the weight of the gel as a "fat substitute".

Recipes c., d. and e. study the substitution of fat using preparative methods in which the linear araban is not formed into a gel before being processed with the other ingredients. Batch 1 of each of recipes c., d. and e. effects 50% fat substitution calculated on the basis of a 20% gel of a linear araban, whilst batch 2 of each effects 75% substitution calculated on the same basis.

a. Low Fat Spread

Gently melt 25 g butter with 25 g linear araban gel, mix well, pour into a container, seal and store in refrigerator.

The sample hardened on cooling without separating and yet retained a texture that was quite spreadable straight from the refrigerator. The product had an acceptable buttery taste.

b. Sponge Cake

Three different cake mixes were prepared with the following ingredients:

|  | Mix 1 | Mix 2 | Mix 3 (control) |
| --- | --- | --- | --- |
| Linear araban gel | 25 g | 12.5 g | — |
| Margarine | — | 12.5 g | 25 g |
| Granulated sugar | 25 g | 25 g | 25 g |
| Egg (beaten) | 25 g | 25 g | 25 g |
| White self raising flour | 25 g | 25 g | 25 g |

The mixes were prepared using an "all-in-one" method, using an electric hand mixer.

Individual cakes were cooked in a microwave oven and an acceptable product was formed. The cakes kept well when covered in cling film for 4 days.

Mix 2 gave cakes with a lighter texture than mix 1, whilst the fullest volume was obtained with mix 3.

c. Ice cream

Three different batches were prepared with the indicated ingredients.

|  | Control wt. % | Batch 1 wt. % | Batch 2 wt. % |
| --- | --- | --- | --- |
| Hydrogenated palm kernel oil | 10.0 | 5.0 | 2.5 |
| Linear araban | — | 1.0 | 1.5 |
| Skim milk powder | 11.0 | 11.0 | 11.0 |
| Sugar | 14.0 | 14.0 | 14.0 |
| Glycerol monostearate | 0.25 | 0.25 | 0.25 |
| Locust bean gum | 0.18 | 0.18 | 0.18 |
| K-carrageenan | 0.02 | 0.02 | 0.02 |
| Vanilla | 0.05 | 0.05 | 0.06 |
| Water | 64.5 | 68.5[1] | 70.5[2] |

[1]Includes 4 wt. % water required to form 20% gel from linear araban.
[2]Includes 6 wt. % water required to form 20% gel from linear araban.

Method

The ice cream of the control batch was prepared using a conventional procedure. Batches 1 and 2 were prepared by weighing the linear araban powder and water into the pasteuriser/mixing tank of the apparatus used and stirring the mix until a temperature of 80° C. was reached to ensure the linear araban was pasteurised. The mix was cooled to 40°–50° C. and the remaining ingredients added under stirring, before the mix was repasteurised and then processed into ice cream using the same conventional procedure adopted for the control.

Results

Batch 1 was very similar to the control in terms of firmness, scoopability, smoothness and degree of aeration. Batch 2 was gritty in texture because of ice crystals and had an undesirably high rate of melting. Batch 1 appeared to be an acceptable product.

d. Mousse

Three different batches were prepared with the indicated ingredients.

|  | Control wt. % | Batch 1 wt. % | Batch 2 wt. % |
| --- | --- | --- | --- |
| Hydrogenated palm kernel oil | 7.0 | 3.5 | 1.75 |
| Linear araban | — | 0.7 | 1.05 |
| Skim milk powder | 11.5 | 11.5 | 11.05 |
| Sugar | 12.0 | 12.0 | 12.0 |
| Gelatin | 2.0 | 2.0 | 2.0 |
| Glycerol monostearate | 0.5 | 0.5 | 0.5 |
| Flavour and colour | 0.05 | 0.05 | 0.05 |
| Water | 66.95 | 69.75[3] | 71.15[4] |

[3]Includes 2.8 wt. % water required to form 20% gel from linear araban.
[4]Includes 4.2 wt. % water required to form 20% gel from linear araban.

Method

The mousse of the control batch was prepared using a conventional procedure. Batches 1 and 2 were prepared by a similar procedure in which the water and linear araban powder were weighed into the pasteuriser/mixing tank of the apparatus used and pasteurised prior to the addition of the other ingredients according to the conventional procedure. After the other ingredients had been added, the mix was again pasteurised before the conventional procedure was followed.

Half of each batch was frozen at −18° C. and half was stored in a chill room at 5° C. The frozen and chilled samples were assessed separately. The frozen mousse was defrosted for 1 hour before being assessed.

Results

The chilled samples of both batches 1 and 2 were very similar to the control in terms of smoothness, scoopability and firmness. However, batch 2 was more difficult to aerate. Both batches were considered acceptable when chilled.

The defrosted frozen sample of batch 1 was very similar to the control and was acceptable. However, batch 2 was not easy to scoop out of the container when frozen and defrosted (splitting occured).

e. Toffee

Three different batches were prepared with the indicated ingredients.

|  | Control wt. % | Batch 1 wt. % | Batch 2 wt. % |
| --- | --- | --- | --- |
| Sugar | 27.9 | 27.9 | 27.9 |
| Liquid glucose syrup | 27.9 | 27.9 | 27.9 |
| Skimmed condensed milk | 27.9 | 27.9 | 27.9 |
| Hydrogenated palm kernel oil | 11.2 | 5.6 | 2.8 |
| Linear araban | — | 1.12 | 1.68 |
| Salt | 0.4 | 0.4 | 0.4 |
| Water | 4.7 | 9.18[5] | 11.42[6] |

[5]Includes 4.48 wt. % water required to form 20% gel from linear araban.
[6]Includes 6.72 wt. % water required to form 20% gel from linear araban.

Method

The same method was used for all three batches. All the ingredients were premixed and heated to 60° C. under stirring. The mix was then transferred to a toffee cooker and boiled at 123° C. under stirring for 25 minutes, before being poured onto a cold slab to set. The samples were sealed in polythene bags and stored at 20° C.

Results

Both batches 1 and 2 were somewhat dark in colour and harder than the control batch. Batch 2 was more glass-like in appearance and more orange in colour than batch 1 and therefore more unacceptable as a toffee product. The colour and texture of both batch 1 and batch 2 were probably unacceptable, but a lower level of fat substitution would probably result in an acceptable product.

Discussion

Recipes c., d. and e. effect substitution of the oil used in the control batch in proportions of 50% and 75% calculated on the basis of a 20% linear araban gel. However, recipes c. and d. in particular use a substantial quantity of water in addition to the water in the gel. For example, the concentration of linear araban in batch 1 of recipe c. calculated on the basis of the total weight of water plus linear araban is 1.44%; in this respect, it is observed that a 1.44% (w/w) solution of linear araban in water would apparently not gel, but that batch 1 of recipe c. produces an acceptable ice cream.

The explanation for these apparently conflicting findings is not known. However, at least part of the explanation of the effectiveness of apparently very low linear araban concentrations in recipes c. and d. might be that a substantial amount of water is absorbed by the gums and gelatin present in the mixes, so that the free water available to the linear araban is substantially reduced.

Whatever the explanation, recipes c. and d. clearly demonstrate that debranched araban can be effective when used in quantities which, when calculated on the basis of the total water content, would seem to be too low for gel formation. An effective combination of ingredients for any particular product can be determined by trial and error.

Recipes c. and d. in particular also demonstrate that it is not necessary to use debranched araban in the form of a pre-made gel when preparing products using it. Rather, the debranched araban can be dissolved in the mix, gelling presumably taking place in the final product or during a stage in the process when the mix is allowed to stand.

EXAMPLE 6

Preparation of Araban from Sugar Beet

The sugar beet pulp used in this Example is sugar beet cossettes which have passed through a diffuser to extract sugar and then been pressed in a screw press. It will be referred to hereinafter as pulp.

625 liters of water at 60° C. were taken in a stainless steel, steam heated, U trough mixer and heated to 90° C. 200 kg of pulp (at 264 dry matter) and 10.0 kg of powdered lime (at 90% CaO) were added to the mixer. The mixer contents were heated to 95°–98° C. and kept at this temperature for 30 minutes with frequent mixing.

The mixer contents were then transferred to nylon net bags which were pressed in a hydraulic press and the extracted juice (615 liters at pH 12.5 and 3.7% Refractometric Dry Substance (% RDS)) transferred to a stainless steel tank. The pressed extracted pulp (185 kg at 19% Dry Matter) was discarded.

The overall yield of product can be increased by washing the pressed extracted pulp with an equal volume of hot water and combining the wash liquor with the press liquor.

The extracted juice was reheated to 80° C. and then circulated through a static mixer, where it was mixed with carbon dioxide gas, until the pH had dropped to $pH_{20}$ 7.6 ($pH_{20}$ refers to pH at 20° C.) This gassed juice was then transferred to a stainless steel tank and left for 2 hours to allow the solid material, mainly calcium carbonate, to settle.

The settled juice (460 liters at 2.9% RDS) was decanted, by suction, from the mud (147 liters at 7.2% Dry Matter) and filtered through a Manor plate and frame (9"×9"—22.9 cm×22.9 cm) press using 3 frames and 120 g of Dicalite 4308 filter aid. 'Dicalite' is a Trade Mark. Filtration pressure was 50 psi (345 kPa) and filtration time 45 minutes.

The filtered juice (450 liters at 2.8% RDS) was then ultra-filtered at 50° C. using an Amicon DC30 Ultrafilter with twelve S10Y10 spiral cartridges (total membrane area 120 ft$^2$ (11 m$^2$); cellulosic membrane; nominal molecular cut off 10,000) at inlet/outlet pressures of 50/30 psi (345/207 kPa). 'Amicon' is a Trade Mark. The Amicon ultrafilter has a recommended maximum operating temperature of 55° C. This gave 30 kg (18.1% RDS) of retentate and about 420 liters of permeate (1.7% RDS).

The retentate was passed into a spray drier (Spray Processes, Bedford, England) at 12 liter/hour with the inlet temperature 180° C. and the outlet temperature 80° C. to yield the araban as a powder (5 kg).

EXAMPLE 7

Encapsulation of Orange Oil a. Preparation of Emulsion

An aqueous phase was prepared by dispersing araban powder in distilled water with stirring at room temperature. This was a relatively lengthy process in view of the large quantities of solids to be dispersed and the process was complete in 2–3 hours. The dispersed solids were allowed to dissolve fully in the aqueous phase for about 16 hours before use.

An emulsion was prepared by the slow addition of orange oil to the aqueous phase under constant high-speed agitation using a Silverson mixer. When addition of the oil was complete, the resulting coarse emulsion was further processed by being passed through an APV (Crawley, England) Manton-Gaulin homogeniser at a pressure of 1,500 psi (10.3 MPa). This produced a fine emulsion with droplet sizes of less than 10 μm.

A comparative gum arabic emulsion was prepared in the same way.

b. Spray Drying

The emulsions were spray-dried using a pilot-scale spray drier (Type Lab 51, Anhydo, Denmark) designed to process relatively small quantities of product (1–5 liters). Emulsions were pumped using a peristaltic unit (Gilson, Minipuls 2) at constant rate into the atomiser head, which was set to run at around 35,000 rev/min. The inlet air temperature was set at around 200° C. Emulsion was pumped into the atomiser when the outlet air temperatures had reached 75°–80° C. Final outlet temperatures of around 90° C.–100° C. were recorded at the end of spray drying runs. After passing through the drying compartment, powdered product was collected in a cyclone unit. The weights of emulsion processed and corresponding product were recorded.

c. Determination of Orange Oil Content of Encapsulated Product

The major component of orange oil is D-limonene and this was used to determine the orange oil content of spray-dried, encapsulated products.

Samples of spray-dried product (around 0.1 g accurately weighed) were dispersed and dissolved in 50 ml ultra high quality water from an Elga TM purification unit. The components of orange oil were extracted into two volumes of chloroform (2×20 ml); the volumes were pooled and made up to 50 ml with chloroform.

Standard orange oil and D-limonene solutions in chloroform were prepared in the concentration range 0.01–0.1% (w/v).

Samples (1 µl) of extracted orange oil, together with orange oil and D-limonene standard solutions, were injected on to the column of a gas chromatograph (5880 A Series, Hewlett Packard ®). The column was a high-performance, cross-linked methyl silicone capillary column (12 meter) operating at 75° C. The carrier gas was nitrogen and an injector temperature of 200° C. was used. The flame-ionisation detector operated at 250° C. Under these conditions, the components of orange oil were readily separated, and the D-limonene content was expressed in terms of peak area. A calibration curve showing the relationship between peak area for the D-limonene component and the concentration of orange oil in chloroform solution was constructed. The conversion factor from this curve was used to estimate the orange oil content of chloroform extracts of one group of spray-dried encapsulated products that were processed on the GC chromatograph at the same time as the standards. In a second series of experiments, the remainder of the spray-dried products were processed together with standards that yielded a slightly different conversion factor. The encapsulation efficiencies of both arabic and araban were defined as the actual oil contents of the spray-dried products expressed as a percentage of the maximum possible oil contents calculated from the polysaccharide/oil ratios.

d. Results

Emulsions containing orange oil (10% of emulsion) and both arabic and araban (30% and 40% of aqueous phase) were prepared. In addition, emulsions containing higher levels of orange oil (15% and 20% of emulsion) were prepared using 40% araban solutions.

These emulsions were spray-dried using the conditions shown in Table I. The inlet air temperature was selected whilst the outlet temperature was dependent on the flow rate of the emulsion into the spray drier. The recovery of spray-dried product was low (less than 20%) in all cases.

The orange oil contents of the spray-dried products were readily determined from the D-limonene component of the chloroform extracts. The calibration curve showing the relationship between the D-limonene peak area and the concentration of orange oil in chloroform solution was linear over the range of concentration investigated. The orange oil contents of the spray-dried products, calculated using the appropriate conversion factors, are shown in Table II. Duplicate values were obtained for all emulsion compositions except that containing 40% arabic/10% oil, for which five values of oil content were obtained. The differences between replicate determinations are probably due to incomplete extraction of the orange oil into the chloroform phase.

However, the oil contents of araban-encapsulated products are very similar to those of arabic-encapsulated products. An increase in the oil/araban ratio in the emulsion did not significantly affect the oil content of the spray-dried products, although encapsulation efficiency was diminished.

The encapsulation efficiency of araban was similar to that of gum arabic (Table III). Well over half the orange oil was encapsulated by both polysaccharides at the 30% and 40% levels (of polysaccharide in water). Only at very high oil content (20% of emulsion) did the encapsulation efficiency significantly diminish.

The relatively low yield of encapsulated product achieved in the spray-drying experiments was partly due to the high proportion of product that adhered to the inside walls of the spray-drying chamber. These losses were in part due to the release of some oil on the chamber wall in line with the plane of the rotating atomiser head. This was probably the result of high-impact collisions of larger spray-dried particles with the wall after leaving the atomiser head. It would be expected that these losses would be considerably reduced in large-scale industrial spray drying equipment in which the chamber volumes and distances between chamber walls and atomiser heads are much greater.

Further improvements in recovery would be obtained by using multi-cyclone recovery units instead of the single unit used in these experiments.

TABLE 1

Conditions used for spray-drying orange oil emulsions in gum arabic and araban solutions.

| Emulsion Composition | Inlet temp (°C.) | Outlet temp (°C.) | Flow rate (g/min) | Product yield (%) |
|---|---|---|---|---|
| 30% arabic/ 10% oil | 210 | 90 | 53 | 21 |
| 40% arabic/ 10% oil | 210 | 100 | 20 | + |
| 30% araban/ 10% oil | 210 | 90 | 52 | 16 |
| 40% araban/ 10% oil | 210 | 100 | 22 | 18 |
| 40% araban/ 15% oil | 200 | 100 | 26 | 16 |
| 40% araban/ 20% oil | 205 | 115 | 23 | 20 |

+ some product was lost in this experiment and product yield was not calculated.

TABLE II

Orange oil contents of various spray-dried, encapsulated products as determined by gas chromatography

| Emulsion composition | Spray-dried sample (g) | Limonene peak area | Orange oil in CHCl₃ extract (% w/w) | Orange oil in sample (% w/w) |
|---|---|---|---|---|
| 30% arabic/ 10% oil | (1) 0.1025 | 2118 | 0.0287 + | 14.0 |
|  | (2) 0.1041 | 2807 | 0.0380 + | 18.3 |
| 30% araban/ 10% oil | (1) 0.1030 | 2623 | 0.0355 + | 17.2 |
|  | (2) 0.1053 | 2977 | 0.0403 + | 19.1 |
| 40% arabic/ 10% oil | (1) 0.1011 | 2013 | 0.0273 + | 13.5 |
|  | (2) 0.1034 | 1708 | 0.0231 + | 11.2 |
|  | (3) 0.1014 | 2356 | 0.0279 + + | 13.8 |
|  | (4) 0.1054 | 2786 | 0.0330 + + | 15.7 |
|  | (5) 0.1037 | 1983 | 0.0235 + + | 11.3 |
| 40% araban/ 10% oil | (1) 0.1061 | 2409 | 0.0285 + + | 13.4 |
|  | (2) 0.1036 | 2187 | 0.0259 + + | 12.5 |
| 40% araban/ 15% oil | (1) 0.1040 | 2860 | 0.0339 + | 16.3 |
|  | (2) 0.1065 | 3066 | 0.0363 + + | 17.0 |
| 40% araban/ | (1) 0.1062 | 2516 | 0.0298 + + | 14.0 |

TABLE II-continued

Orange oil contents of various spray-dried, encapsulated products as determined by gas chromatography

| Emulsion composition | Spray-dried sample (g) | Limonene peak area | Orange oil in CHCl$_3$ extract (% w/w) | Orange oil in sample (% w/w) |
|---|---|---|---|---|
| 20% oil | (2) 0.1047 | 2588 | 0.0306 ++ | 14.6 |

+ conversion factor 1.35 10$^{-5}$ (area/%)
++ conversion factor 1.18 10$^{-5}$ (area/%)

TABLE III

A comparison of the encapsulation efficiencies of araban and gum arabic used in a spray-dried, encapsulated orange oil product.

| Emulsion composition | Actual oil content of product (% w/w) | Max. theoretical oil content (% w/w) | Actual × 100 (%) max. theoretical |
|---|---|---|---|
| 30% arabic/ 10% oil | 1) 14.0 | 28.5 | 49 |
| | 2) 18.3 | 28.5 | 64 |
| 30% araban/ 10% oil | 1) 17.2 | 28.5 | 60 |
| | 2) 19.1 | 28.5 | 67 |
| 40% arabic/ 10% oil | 1) 13.5 | 23.0 | 59 |
| | 2) 11.2 | 23.0 | 49 |
| | 3) 13.8 | 23.0 | 60 |
| | 4) 15.7 | 23.0 | 68 |
| | 5) 11.3 | 23.0 | 49 |
| 40% araban/ 10% oil | 1) 13.4 | 23.0 | 58 |
| | 2) 12.5 | 23.0 | 54 |
| 40% araban 15% oil | 1) 16.3 | 31.1 | 52 |
| | 2) 17.0 | 31.1 | 55 |
| 40% araban/ 20% oil | 1) 14.0 | 38.5 | 36 |
| | 2) 14.6 | 38.5 | 38 |

EXAMPLE 8

Stability of Encapsulated Orange Oil

The results of re-analysis of the spray-dried encapsulated orange oil are shown in Table IV. Samples were stored in polythene bags at room temperature in the dark for 28 weeks before being re-analysed, using the same GC method as before (based on quantification of D-limonene).

Conclusion

Araban appears at least as good as gum arabic in its capacity to encapsulate orange oil. However, spray-dried powders prepared with araban are more stable during storage than those prepared with gum arabic.

TABLE IV

| Sample | % Oil encapsulated Initial | % Oil encapsulated At 28 weeks | Fall on storage (%) |
|---|---|---|---|
| Arabic 30%/ Oil 10% | 71.2 | 40.0 | 44 |
| Araban 30%/ Oil 10% | 70.9 | 66.7 | 6 |
| Arabic 40%/ Oil 10% | 62.5 | 47.4 | 24 |
| Araban 40%/ Oil 10% | 62.6 | 56.1 | 10 |
| Araban 40%/ Oil 15% | 53.3 | 43.7 | 18 |
| Araban 40%/ Oil 20% | 37.1 | 37.7 | — |

What is claimed is:

1. A method of forming an aqueous gel of gel-forming debranched araban, comprising:
    forming an aqueous mixture of gel-forming debranched araban;
    dissolving the debranched araban at an elevated temperature;
    cooling the resultant solution for a time sufficient to form a gel.

2. The method of claim 1 wherein the debranched araban is debranched sugar beet araban and is present in an amount of at least 8% by weight, based on the weight of the gel.

3. The method of claim 1 wherein the debranched sugar beet araban is present in an amount of 12% to 20% by weight, based on the weight of the gel.

4. A process for the preparation of a food which food ordinarily comprises an oil or a fat, including the step of:
    adding a gel-forming debranched araban as a substitute for said oil or fat.

5. The process of claim 4 wherein the gel-forming debranched araban is more than 80% debranched as determined by proton resonance nmr.

6. The process of claim 4 wherein the gel-forming debranched araban is at least 98% debranched as determined by proton resonance nmr.

7. The process of claim 4 wherein the gel-forming debranched araban in an amount of at least 0.7% by weight based on the weight of the food.

8. The process of claim 4 wherein the gel-forming debranched araban is debranched sugar beet araban.

9. The process of claim 4 wherein the debranched araban is debranched crude sugar beet araban, said debranched araban comprising no more than 90% by weight or arabinose.

10. An aqueous emulsion of debranched araban and an oil or a fat wherein the debranched araban constitutes from 20% to 50% by weight of the aqueous phase.

11. An aqueous emulsion of debranched araban and an oil or a fat wherein the fat or oil constitutes from 10% to 30% by weight of the emulsion.

12. A method of preparing a gel-forming debranched araban, comprising:
    extracting a crude araban of which no more than 90% by weight is arabinose, by extraction from a plant of the species *Beta vulgaris* under alkaline conditions;
    neutralizing the alkaline solution;
    ultrafiltering the solution;
    incubating said crude araban with α-L-arabinofuranosidase until the crude araban is more than 80% debranched as determined by proton resonance nmr; and
    isolating the debranched araban to obtain a gel-forming debranched araban.

13. The method of claim 12 wherein the debranched araban is more than 98% debranched.

14. The method of claim 12 wherein said plant is sugar beet.

15. The method of claim 13 or 14 wherein the crude araban is decolorized by bleaching with hydrogen peroxide following the neutralization step.

16. The method of claim 15 wherein the neutralizing step is carried out using carbon dioxide.

17. An oil or fat encapsulated in debranched araban.

18. The oil or fat encapsulated in debranched araban of claim 17 wherein the debranched araban comprises no more than 90% by weight arabinose.

19. A method of encapsulating a fat or oil, comprising the steps of:
    forming an aqueous emulsion of debranched araban and the fat or oil; and spray drying the aqueous emulsion.

20. The method of claim 19 wherein the debranched araban constitutes from 20% to 50% by weight of the aqueous phase of the emulsion.

21. The method of claim 19 wherein the fat or oil constitutes from 10% to 30% by weight of the emulsion.

* * * * *

UNITED STATES PATENT AND TRADEMARK OFFICE
CERTIFICATE OF CORRECTION

PATENT NO. : 5,250,306
DATED : October 5, 1993
INVENTOR(S) : Barry V. McCleary, Julian M. Cooper & Edward L. Williams It is certified that error appears in the above-indentified patent and that said Letters Patent is hereby corrected as shown below:

Column 22, lines 1 & 2, (claim 1) --and-- should be inserted after "temperature;"

Column 22, line 24, (claim 7) --is added-- should be inserted after "debranched araban"

Column 22, line 31, (claim 9) --or-- should read "of"

Signed and Sealed this

Tenth Day of May, 1994

*Attest:*

BRUCE LEHMAN

*Attesting Officer*     *Commissioner of Patents and Trademarks*